United States Patent
Bigelow, Jr.

(10) Patent No.: US 6,787,350 B2
(45) Date of Patent: Sep. 7, 2004

(54) SYSTEM AND METHOD FOR MOLD DETECTION

(76) Inventor: Floyd E. Bigelow, Jr., 18003 Spellbrook, Houston, TX (US) 77084

( * ) Notice: Subject to any disclaimer, the term of this patent is extended or adjusted under 35 U.S.C. 154(b) by 0 days.

(21) Appl. No.: 10/083,980

(22) Filed: Feb. 27, 2002

(65) Prior Publication Data

US 2003/0162286 A1 Aug. 28, 2003

(51) Int. Cl.[7] ................................................ C12M 1/34
(52) U.S. Cl. ................... 435/287.7; 435/288.7; 435/309.1; 435/805; 435/808
(58) Field of Search .................... 435/287.1, 287.7, 435/288.7, 309.1, 805, 808, 30

(56) References Cited

U.S. PATENT DOCUMENTS

| | | |
|---|---|---|
| 2,041,731 A | 5/1936 | Wallerstein |
| 2,106,896 A | 2/1938 | McCulloch |
| 3,966,551 A | 6/1976 | Monsheimer .................. 195/6 |
| 3,976,495 A | 8/1976 | Buckman ...................... 435/34 |
| 4,288,498 A | 9/1981 | Scribner, Jr. ................. 428/473 |
| 4,293,559 A | 10/1981 | Buckman .................... 424/270 |
| 4,314,027 A | 2/1982 | Stahr .......................... 435/34 |
| 4,322,475 A | 3/1982 | Lewis et al. ................. 428/411 |
| 4,340,437 A | 7/1982 | Rogers ........................ 156/224 |
| 4,983,511 A * | 1/1991 | Geiger et al. .................. 435/6 |
| 5,011,499 A | 4/1991 | Rathfelder .................. 8/94.33 |
| 5,409,838 A * | 4/1995 | Wickert ......................... 436/8 |
| RE34,986 E | 7/1995 | Rathfelder .................. 8/94.33 |
| 5,571,443 A | 11/1996 | Dalton et al. ............... 252/8.57 |
| 5,856,118 A * | 1/1999 | Dalmasso ..................... 435/31 |
| 5,912,115 A * | 6/1999 | Hyman et al. ................. 435/4 |

* cited by examiner

Primary Examiner—David A. Redding
(74) Attorney, Agent, or Firm—Guy McClung

(57) ABSTRACT

A mold indicator having a piece of leather, a covering over at least a first portion of the piece of leather, at least a second portion of the piece of leather not covered by the covering exposable to an environment around the mold indicator. The mold indicator including the piece of leather is untanned. The mold indicator including the covering is a layer includes anti-mold agent.

15 Claims, 2 Drawing Sheets

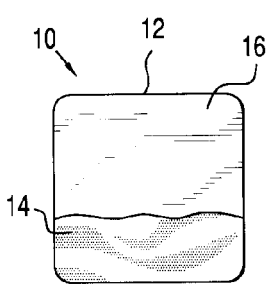
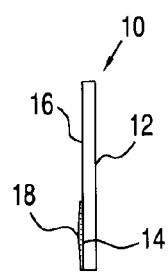
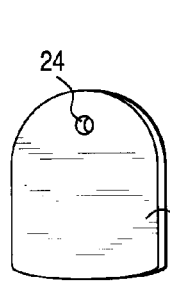
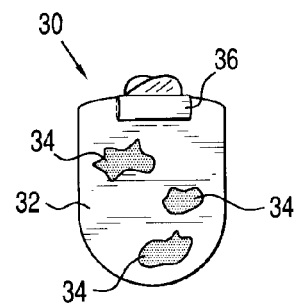
FIG.1A  FIG.1B  FIG.2  FIG.3
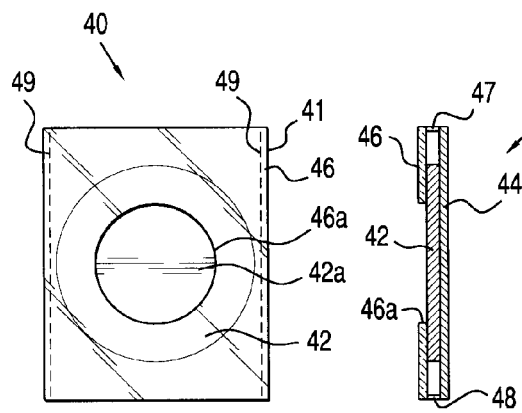
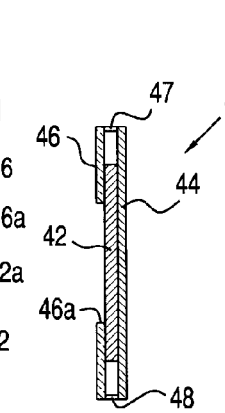
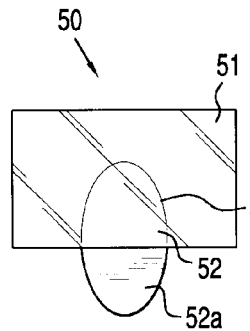
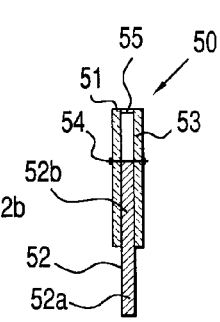
FIG.4A  FIG.4B  FIG.5A  FIG.5B
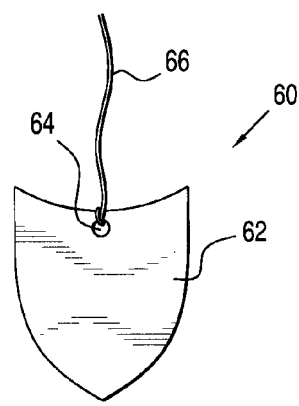
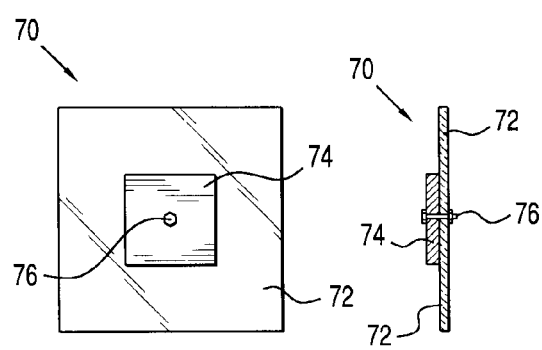
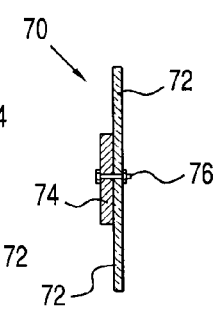
FIG.6  FIG.7A  FIG.7B

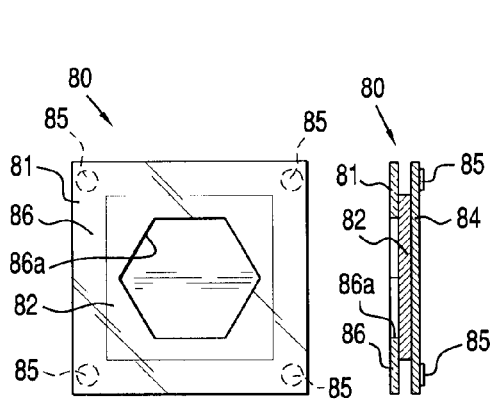
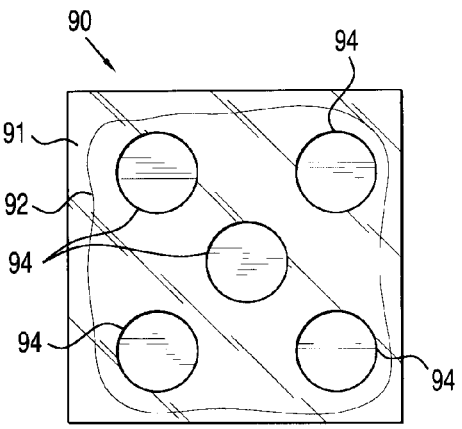
FIG.8A  FIG.8B  FIG.9
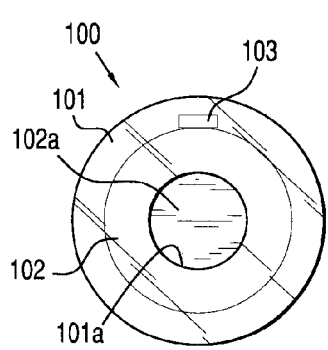
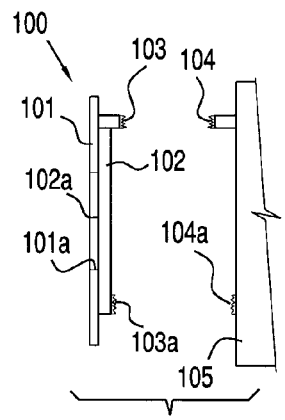
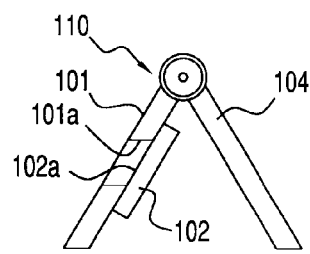
FIG.10A  FIG.10B  FIG.11
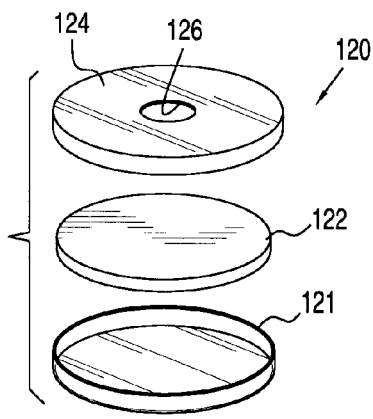
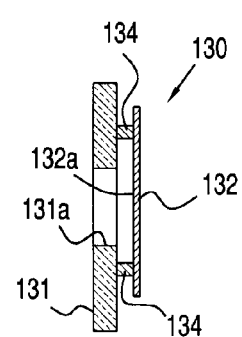
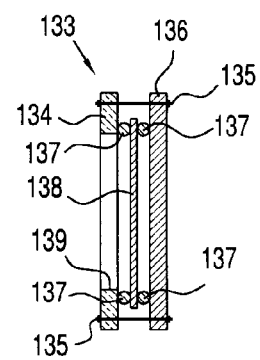
FIG.12  FIG.13A  FIG.13B

SYSTEM AND METHOD FOR MOLD DETECTION

BACKGROUND OF THE INVENTION

1. Field of the Invention

This invention is directed to systems, devices and methods for mold detection and, in at least certain embodiments, apparatus and methods with exposed leather on which growing mold is easily discerned.

2. Description of Related Art

Fungus, mold, and mildew grow in many environments and can present a serious health hazard. Often building and structures with mold, etc. have to be decontaminated or, in worst cases, demolished. In many cases when the presence of mold, etc. is detected, the mold, etc. has spread significantly.

There has long been a need, recognized by the present inventor, for a simple and practical system for indicating the presence of and the growth of mold. There has long been a need for such a system that is reliable and with which mold is easily discerned.

SUMMARY OF THE PRESENT INVENTION

The present invention discloses, in certain aspects, apparatus with a piece of leather in which at least a portion of the leather is exposed to the air. Mold will often begin growing, or grow more rapidly, on leather before it begins growing on other things or items at the same location, or the growth of mold on leather will be more easily discernible than mold growing on other nearby things. The leather may be raw leather, semi-tanned, or tanned leather.

In one aspect a mounting is provided for a piece of leather so that it is easily positionable at a desired place. In one particular embodiment, a piece of clear glass or plastic is placed over a portion of a piece of leather so that another portion of the leather is not covered by the glass or plastic. Thus a visible contrast is provided when mold begins to grow on the exposed part of the leather. In one aspect, relatively light colored leather is used or leather that has not been colored so that the contrast between leather without mold on it and leather with mold on it is easy to see. In certain aspects a picture frame apparatus is used for mounting a piece of leather, and an outer exterior pane of glass or clear plastic has at least one or more cut-out parts so that leather mounted in the frame has one or more parts exposed to the air around the frame.

In other aspects relatively flat cases or containers are provided according to the present invention which have at least part of at least one side made of clear material so that a piece of leather can be seen within the container. One or more cut-out portions of the container provide an area at which part of the leather is exposed to the air. Mold that grows on the exposed part is readily discernible. Alternatively, as may be the case with the frame mentioned above, no clear plastic or clear glass is used and the only part of the leather that can be seen is the exposed part. In other aspects the case, frame or container is made so that air circulates between structural members and leather therein is exposed to the air.

With any embodiment of the present invention, any suitable fastening and/or attaching apparatus and/or device may be used to fasten and/or attach—permanently or releasably—a mold indicator according to the present invention to another thing or item. For example, but not by way of limitation, one or more magnets may be used with apparatus according to the present invention to releasably connect a mold indicator to a window, window frame, door, or door frame; to the grill of an air conditioning or heater system; or to an appliance such as a washer, dryer, refrigerator, cooler, or fan. Releasably cooperating hook-and-loop fastener material or any suitable adhesive material and/or suction cup or apparatus may also be used for such attachment and/or connection.

It is, therefore, an object of at least certain preferred embodiments of the present invention to provide:

New, useful, unique, efficient, nonobvious systems and methods for indicating the growth and/or presence of mold;

Such a systems and methods that use a piece of leather to facilitate mold indication and detection;

Such systems and methods that use a mounting device or apparatus to hold a piece of leather and which, in at least certain aspects, provide a view of a covered or protected part of a piece of leather and/or of an exposed part to provide a visible contrast between leather on which mold is not growing, or on which it is not growing relatively quickly, and leather on which mold is growing or on which mold is growing relatively quickly; and Such systems and methods which use frames, mounts, etc. that include connection or attachment apparatus for permanently or releasably locating or mounting the mold indicator in a desired area or location.

Certain embodiments of this invention are not limited to any particular individual feature disclosed here, but include combinations of them distinguished from the prior art in their structures and functions. Features of the invention have been broadly described so that the detailed descriptions that follow may be better understood, and in order that the contributions of this invention to the arts may be better appreciated. There are, of course, additional aspects of the invention described below and which may be included in the subject matter of the claims to this invention. Those skilled in the art who have the benefit of this invention, its teachings, and suggestions will appreciate that the conceptions of this disclosure may be used as a creative basis for designing other structures, methods and systems for carrying out and practicing the present invention. The claims of this invention are to be read to include any legally equivalent devices or methods which do not depart from the spirit and scope of the present invention.

The present invention recognizes and addresses the previously-mentioned problems and long-felt needs and provides a solution to those problems and a satisfactory meeting of those needs in its various possible embodiments and equivalents thereof. To one of skill in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

FIG. 1A is a front view of a mold indicator according to the present invention. FIG. 1B is a side view of the mold indicator of FIG. 1A.

FIG. 2 is a perspective view of a mold indicator according to the present invention.

FIG. 3 is a front view of a mold indicator according to present invention.

FIG. 4A is a front view of a system according to the present invention. FIG. 4B is a cross-section view of the mold indicator of FIG. 4A.

FIG. 5A is a front view of a system according to the present invention. FIG. 5B is a cross-section view of the system of FIG. 5A.

FIG. 6 is a front view of a system according to the present invention.

FIG. 7A is a front view of a system according to the present invention. FIG. 7B is a cross-section view of the system of FIG. 7A.

FIG. 8A is a front view of a system according to the present invention. FIG. 8B is a cross-section view of the system of FIG. 8A.

FIG. 9 is a front view of a system according to the present invention.

FIG. 10A is a front view of a system according to the present invention. FIG. 10B is a side view of the system of FIG. 10A.

FIG. 11 is a side view of a system according to the present invention.

FIG. 12 is an exploded view of a system according to the present invention.

FIGS. 13A and 13B are side cross-section views of systems according to the present invention.

DESCRIPTION OF EMBODIMENTS PREFERRED AT THE TIME OF FILING FOR THIS PATENT

FIGS. 1A and 1B show a mold indicator 10 according to the present invention which includes a piece of leather 12. The piece of leather 12, as may be the case with any piece of leather in any system disclosed herein according to the present invention, may be any desirable size and thickness. Preferably the leather is untanned, rawhide, or semi-tanned, although any leather may be used. Optionally part 14 of the piece of leather 12 is covered with a clean layer, film, coating, or laminate 18 that isolates that part's surface from ambient air around the piece of leather 12. Optionally the layer, etc. may contain anti-fungal, mildew-inhibiting, and/or mold-inhibiting agent(s). Thus, mold will grow on a part 16 that is not so covered or mold will grow more quickly on the uncovered part 16 than on the covered part 14; and such difference in growth will be visually discernible.

FIG. 2 shows a piece of mold indictor 20 according to the present invention which includes a piece of leather 22 having a hold 24 for mounting the mold indicator 20 with a nail, screw, or bolt, etc. to a wall, ceiling, structure, appliance, furniture etc. or for passing a rape, cord, line or twine etc. through the hole 24 to use the rope, etc. to position the mold indicator 20 in a desirable location. A layer, etc. 18 as in FIG. 1A may be used on the piece of leather 22.

FIG. 3 shows a mold indicator 30 according to the present invention which has a piece of leather 32 to which a clip 36 has been releasably attached. The clip 36 may be used to position or mount the mold indicator 30 in a desired location. Optionally, multiple areas 34 of the leather 32 are coated, etc. with material like that of the layer 18, FIG. 1B. It is within the scope of this invention to use any desired member of such areas 34 of any desired shape and/or size on any piece of leather in any system according to the present invention.

FIGS. 4A and 4B show a mold indicator system 40 according to the present invention which has a frame 41 with a front piece 46 made preferably of clear material such as clear plastic or glass with a hole 46a therethrough. Between a back member 44 and the front piece 46 is a piece of leather 42, part 42a of which is exposed within the boundary of the hole 46a. The front piece 46 and the back member 44 may, optionally, be connected by screws or bolts (not shown) or by members 47, 48 (top and bottom, respectfully) and/or by side members 49.

The members 47, 48 and side members 49 may be sized and configured to seal off the top, bottom, and sides of the frame 41 or they may be sized to allow air to circulate into the frame's interior. Any suitable tape, glue, adhesive etc. may (as with any parts in any system herein) be used to hold parts together.

FIG. 6 shows a mold indicator 60 according to the present invention which includes a piece of leather 62 with a hole 64 therethrough. A string 66 is tied through the hole 64. The string 66 may be used to connect the mold indicator 60 to any suitable thing or structure.

FIG. 7A shows a mold indicator system 70 according to the present invention which has a piece of leather 72. A clear piece of material 74 is attached over part of the piece of leather 72, e.g. with glue or adhesive and/or with a bolt 76 that extends through the leather 72 and material 74. Any suitable connector, nail, shaft, dowel, screw, etc. may be used instead of the bolt 76.

FIGS. 8A and 8B show a mold indicator system 80 according to the present invention which has a piece of leather 82 in a frame 81. A front piece 86 has a hole 86a therethrough via which part 82a of the piece of leather 82 is exposed. Magnets 85 (one, two, or more may be used) are mounted on a rear part 84 to provide releasable mounting of the mold indicator system 80 to metal. Front and rear frame parts may be connected together in any way described herein.

FIG. 9 shows a mold indicator system 90 according to the present invention that includes a piece of clear material 96 with multiple holes 94 therethrough. The piece of clear material 96 is mounted over a piece of leather 92. As with any piece of clear material in any system according to the present invention, any suitable number of hole(s) 94 of any desired shape and size may be used.

FIGS. 10A and 10B show a mold indicator system 100 according to the present invention which has a piece of clear material 101 with a hole 101a therethrough. A piece of leather 102 is mounted behind the hole 101a with part of the leather 102a exposed through the hole 101a. A piece 103 of hook-and-loop releasably cooperating fastener material is affixed to the rear of the piece of clear material 101. A corresponding mating piece 104 of such material is affixed to any item 105 (which may be any thing on or to which a mold indicator according to the present invention may be mounted or connected). Thus the mold indicator system 100 is releasably connected to the item 105. One, two, three, four or more pieces of material 103 may be used (as is the case with any system according to the present invention). Optionally, material 103a (like the material 103) on the piece of leather 102 mates with material 104a (like the material 104) on the item 105. Optionally one or more magnets (like magnets 85, FIG. 8A) may be used on any piece of leather in any system according to the present invention.

FIG. 11 shows a mold indicator system 110 according to the present invention which has a front piece 101 hingedly connected to a rear piece 104 with a hinge 106. A piece of leather 102 affixed to, adhered to, and/or connected to the front piece 101 has a portion 102a exposed in s hole 101a through the front piece 101.

FIG. 12 shows a mold indicator system 120 according to the present invention which includes a bottom part 1121 over which is releasably emplaceable a top part 124. A piece of leather 122 is placed within the bottom part 121 before the top part 124 is put on. Part of the leather 122 is exposed via a hole 126 in the top part 124. The parts are, in one aspect, sized so that the leather is held tightly within the case or container formed by the parts 121, 124. Either or both parts 121, 124 may be made of clear material.

FIG. 13A shows a mold indicator system 130 with a body 131 having an optional hole 131a therethrough. Spacers 134 are connected or affixed to the body 131 and a piece of leather 132 is connected or adhered to the spacers 134. Part 132a of the leather 132 may be viewed through the hole 131a whether the body 131 is made of clear or of opaque material (as may be any part or piece of any system according to the present invention).

FIG. 13B shows a mold indicator 133 according to the present invention which has a front part 134 connected by connectors 135 to a rear part 1136. Spacers 137 abut a piece of leather 138. The piece of leather 138 is viewable through a hole 139 in the front part 134 (whether the front part is clear or opaque). The connectors 135 are shown as bolts, but they may be any connector or joining member disclosed herein. As shown the tops and sides of the mold indicator 133 are open to air flow; optionally, however, they may be closed off to air flow.

In the claims, "mold" refers to any of these things: mold, mildew or fungus.

The present invention, therefore, provides in certain, but not necessarily all embodiments, systems as disclosed herein The present invention, therefore, provides in certain, but not necessarily all embodiments, systems as disclosed herein for The present invention, therefore, provides in certain, but not necessarily all embodiments, systems as disclosed herein for The present invention, therefore, provides in certain, but not necessarily all embodiments, methods for indicating and/or detecting the presence and/or growth of mold using systems as disclosed herein according to the present invention.

In conclusion, therefore, it is seen that the present invention and the embodiments disclosed herein and those covered by the appended claims are well adapted to carry out the objectives and obtain the ends set forth. Certain changes can be made in the subject matter without departing from the spirit and the scope of this invention. It is realized that changes are possible within the scope of this invention and it is further intended that each element or step recited in any of the following claims is to be understood as referring to all equivalent elements or steps. The following claims are intended to cover the invention as broadly as legally possible in whatever form it may be utilized. The invention claimed herein is new and novel in accordance with 35 U.S.C. §102 and satisfies the conditions for patentability in §102. The invention claimed herein is not obvious in accordance with 35 U.S.C. §103 and satisfies the conditions for patentability in §103. This specification and the claims that follow are in accordance with all of the requirements of 35 U.S.C. §112.

What is claimed is:

1. A mold indicator comprising
   a piece of leather,
   a covering over at least a first portion of the piece of leather,
   at least a second portion of the piece of leather not covered by the covering exposable to an environment around the mold indicator, wherein the covering includes an anti-mold agent.

2. The mold indicator of claim 1 wherein the piece of leather is untanned.

3. The mold indicator of claim 1 wherein the piece of leather is rawhide.

4. The mold indicator of claim 1 wherein the covering includes a layer of clear material.

5. The mold indicator of claim 1 wherein the covering includes a film of clear material.

6. The mold indicator of claim 1 further comprising
   the covering comprising a piece of material with at least one hole therethrough through which part of the piece of leather is viewable to see mold growing thereon.

7. The mold indicator of claim 6 wherein the piece of material is translucent so that a difference in mold growth in part of the piece of leather covered by the piece of material and part of the leather within a boundary of the hole is discernible.

8. The mold indicator of claim 6 further comprising
   a back member,
   the piece of leather positioned between the piece of material and the back member.

9. The mold indicator of claim 8 further comprising
   spacer apparatus for spacing the piece of leather apart from the piece of material.

10. The mold indicator of claim 8 further comprising
    spacer apparatus for spacing the piece of leather apart from the back member.

11. The mold indicator of claim 1 wherein the piece of leather has a piece area as viewed from above and the covering has a covering area, the piece area greater than the covering area.

12. The mold indicator of claim 1 wherein the covering is attached to the piece of leather with connector apparatus.

13. The mold indicator of claim 1 wherein the covering has a plurality of holes therethrough each for exposing a portion of the piece of leather.

14. The mold indicator of claim 1 further comprising
    connector apparatus connected to either the covering or to the piece of leather for connecting the mold indicator to another thing.

15. A mold indicator comprising
    a piece of leather,
    a covering over at least a first portion of the piece of leather,
    at least a second portion of the piece of leather not covered by the covering exposable to an environment around the mold indicator,
    wherein the piece of leather is untanned, and
    the covering comprising a piece of material with at least one hole therethrough through which part of the piece of leather is viewable to see mold growing thereon.

* * * * *